United States Patent
Yanai et al.

(10) Patent No.: US 9,556,873 B2
(45) Date of Patent: Jan. 31, 2017

(54) STARTUP SEQUENCE FOR CENTRIFUGAL PUMP WITH LEVITATED IMPELLER

(71) Applicant: TC1 LLC, Pleasanton, CA (US)

(72) Inventors: Masamichi Yanai, Ann Arbor, MI (US); Jeffrey H. Campau, Pinckney, MI (US); Russel J. Corvese, Ann Arbor, MI (US); Jason C. Nanna, Plymouth, MI (US)

(73) Assignee: TC1 LLC, Pleasanton, CA (US)

(*) Notice: Subject to any disclaimer, the term of this patent is extended or adjusted under 35 U.S.C. 154(b) by 386 days.

(21) Appl. No.: 13/778,411

(22) Filed: Feb. 27, 2013

(65) Prior Publication Data

US 2014/0241904 A1 Aug. 28, 2014

(51) Int. Cl.
*F04D 1/00* (2006.01)
*F04D 13/06* (2006.01)
(Continued)

(52) U.S. Cl.
CPC .............. *F04D 1/00* (2013.01); *A61M 1/1015* (2014.02); *A61M 1/1086* (2013.01); *A61M 1/122* (2014.02);
(Continued)

(58) Field of Classification Search
CPC F04D 29/048; F04D 15/0066; F04D 15/0077; F04D 19/042; F04D 29/047; F04D 13/024; F04D 13/06; F04D 13/0633; F04D 15/0088; F04D 19/048; F04D 1/00; F04D 29/0473; F04D 29/428; F04D 29/70; F16C 32/0448; F16C 32/0457; F16C 32/0442; F16C 2360/45; F16C 32/047; F16C 39/02; A61M 1/101; A61M 1/1017
(Continued)

(56) References Cited

U.S. PATENT DOCUMENTS

| 1,093,868 A | 4/1914 | Leighty |
| 2,684,035 A | 7/1954 | Kemp |

(Continued)

FOREIGN PATENT DOCUMENTS

| CN | 1347586 A | 5/2002 |
| CN | 1462344 A | 12/2003 |

(Continued)

OTHER PUBLICATIONS

International Search Report and Written Opinion of PCT/US2014/012448 mailed on Feb. 19, 2014, 8 pages.

(Continued)

*Primary Examiner* — Charles Freay
*Assistant Examiner* — Thomas Cash
(74) *Attorney, Agent, or Firm* — Kilpatrick Townsend & Stockton LLP

(57) ABSTRACT

A centrifugal pump system having an impeller rotating with first and second magnetic structures on opposite surfaces. A levitation magnetic structure is disposed at a first end of a pump housing having a levitating magnetic field for axially attracting the first magnetic structure. A multiphase magnetic stator at a second end of the pump housing generates a rotating magnetic field for axially and rotationally attracting the second magnetic structure. A commutator circuit provides a plurality of phase voltages to the stator. A sensing circuit determines respective phase currents. A controller calculates successive commanded values for the phase voltages during a running state in response to a desired impeller speed and an actual impeller phase. The controller has a startup interval during which the commanded values of the phase voltages are determined in response to a pseudo impeller phase and in response to a ramping gain factor.

15 Claims, 5 Drawing Sheets

(51) Int. Cl.
    *F04D 29/048*     (2006.01)
    *A61M 1/12*     (2006.01)
    *A61M 1/10*     (2006.01)

(52) U.S. Cl.
    CPC ......... *F04D 13/0633* (2013.01); *F04D 29/048* (2013.01); *A61M 1/101* (2013.01)

(58) Field of Classification Search
    USPC .................................. 417/420, 423.1–423.15
    See application file for complete search history.

(56) References Cited

U.S. PATENT DOCUMENTS

| | | |
|---|---|---|
| 3,023,334 A | 2/1962 | Burr et al. |
| 3,510,229 A | 5/1970 | Smith |
| 3,620,638 A | 11/1971 | Kaye et al. |
| 3,870,382 A | 3/1975 | Reinhoudt |
| 3,932,069 A | 1/1976 | Giardini et al. |
| 3,960,468 A | 6/1976 | Boorse et al. |
| 4,149,535 A | 4/1979 | Voider |
| 4,382,199 A | 5/1983 | Isaacson |
| 4,392,836 A | 7/1983 | Sugawara |
| 4,434,389 A | 2/1984 | Langley et al. |
| 4,507,048 A | 3/1985 | Belenger et al. |
| 4,528,485 A | 7/1985 | Boyd, Jr. |
| 4,540,402 A | 9/1985 | Aigner |
| 4,549,860 A | 10/1985 | Yakich |
| 4,645,961 A | 2/1987 | Maisky |
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papatonakos |
| 4,779,614 A | 10/1988 | Moise |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,857,781 A | 8/1989 | Shih |
| 4,888,011 A | 12/1989 | Kung et al. |
| 4,895,557 A | 1/1990 | Moise et al. |
| 4,900,227 A | 2/1990 | Troup lin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 4,995,857 A | 2/1991 | Arnold |
| 5,021,048 A | 6/1991 | Buckholtz |
| 5,078,741 A | 1/1992 | Bramm et al. |
| 5,092,844 A | 3/1992 | Schwartz et al. |
| 5,092,879 A | 3/1992 | Jarvik |
| 5,106,263 A | 4/1992 | Irie |
| 5,106,273 A | 4/1992 | Lemarquand et al. |
| 5,106,372 A | 4/1992 | Ranford |
| 5,112,349 A | 5/1992 | Summers et al. |
| 5,113,304 A | 5/1992 | Ozaki et al. |
| 5,129,883 A | 7/1992 | Black |
| 5,145,333 A | 9/1992 | Smith |
| 5,147,186 A | 9/1992 | Buckholtz |
| 5,190,528 A | 3/1993 | Fonger et al. |
| 5,201,679 A | 4/1993 | Velte et al. |
| 5,211,546 A | 5/1993 | Isaacson et al. |
| 5,229,693 A | 7/1993 | Futami et al. |
| 5,275,580 A | 1/1994 | Yamazaki |
| 5,290,227 A | 3/1994 | Pasque |
| 5,290,236 A | 3/1994 | Mathewson |
| 5,300,112 A | 4/1994 | Barr |
| 5,306,295 A | 4/1994 | Kolff et al. |
| 5,312,341 A | 5/1994 | Turi |
| 5,313,128 A | 5/1994 | Robinson et al. |
| 5,332,374 A | 7/1994 | Kricker et al. |
| 5,346,458 A | 9/1994 | Afield |
| 5,350,283 A | 9/1994 | Nakazeki et al. |
| 5,354,331 A | 10/1994 | Schachar |
| 5,360,445 A | 11/1994 | Goldowsky |
| 5,370,509 A | 12/1994 | Golding et al. |
| 5,376,114 A | 12/1994 | Jarvik |
| 5,385,581 A | 1/1995 | Bramm et al. |
| 5,405,383 A | 4/1995 | Barr |
| 5,449,342 A | 9/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,519,270 A | 5/1996 | Yamada et al. |
| 5,533,957 A | 7/1996 | Aldea |
| 5,569,111 A | 10/1996 | Cho et al. |
| 5,575,630 A | 11/1996 | Nakazawa et al. |
| 5,588,812 A | 12/1996 | Taylor et al. |
| 5,595,762 A | 1/1997 | Derrieu et al. |
| 5,611,679 A | 3/1997 | Ghosh et al. |
| 5,613,935 A | 3/1997 | Jarvik |
| 5,630,836 A | 5/1997 | Prem et al. |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,708,346 A | 1/1998 | Schob |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,795,074 A | 8/1998 | Rahman et al. |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,843,129 A | 12/1998 | Larson et al. |
| 5,851,174 A | 12/1998 | Jarvik et al. |
| 5,853,394 A | 12/1998 | Tolkoff et al. |
| 5,868,702 A | 2/1999 | Stevens et al. |
| 5,868,703 A | 2/1999 | Bertolero et al. |
| 5,890,883 A | 4/1999 | Golding et al. |
| 5,911,685 A | 6/1999 | Siess et al. |
| 5,917,295 A | 6/1999 | Mongeau |
| 5,917,297 A | 6/1999 | Gerster et al. |
| 5,921,913 A | 7/1999 | Siess |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Israelev |
| 5,941,813 A | 8/1999 | Sievers et al. |
| 5,947,703 A | 9/1999 | Nojiri et al. |
| 5,951,263 A | 9/1999 | Taylor et al. |
| 5,964,694 A | 10/1999 | Siess et al. |
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |
| 6,053,705 A | 4/2000 | Schob et al. |
| 6,058,593 A | 5/2000 | Siess |
| 6,066,086 A | 5/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,082,900 A | 7/2000 | Takeuchi et al. |
| 6,083,260 A | 7/2000 | Aboul-Hosn et al. |
| 6,086,527 A | 7/2000 | Talpade |
| 6,100,618 A | 8/2000 | Schoeb et al. |
| 6,123,659 A | 9/2000 | leBlanc et al. |
| 6,123,726 A | 9/2000 | Mori et al. |
| 6,139,487 A | 10/2000 | Siess |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |

(56) References Cited

U.S. PATENT DOCUMENTS

| | | |
|---|---|---|
| 6,171,078 B1 | 1/2001 | Schob |
| 6,176,822 B1 | 1/2001 | Nix et al. |
| 6,176,848 B1 | 1/2001 | Rau et al. |
| 6,179,773 B1 | 1/2001 | Prem et al. |
| 6,190,304 B1 | 2/2001 | Downey et al. |
| 6,200,260 B1 | 3/2001 | Bolling |
| 6,206,659 B1 | 3/2001 | Izraelev |
| 6,222,290 B1 | 4/2001 | Schob et al. |
| 6,227,797 B1 | 5/2001 | Watterson et al. |
| 6,227,820 B1 | 5/2001 | Jarvik |
| 6,234,772 B1 | 5/2001 | Wampler et al. |
| 6,234,998 B1 | 5/2001 | Wampler |
| 6,245,007 B1 | 6/2001 | Bedingham et al. |
| 6,247,892 B1 | 6/2001 | Kazatchkov et al. |
| 6,249,067 B1 | 6/2001 | Schob et al. |
| 6,254,359 B1 | 7/2001 | Aber |
| 6,264,635 B1 | 7/2001 | Wampler et al. |
| 6,268,675 B1 | 7/2001 | Amrhein |
| 6,276,831 B1 | 8/2001 | Takahashi et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,320,731 B1 | 11/2001 | Eeaves et al. |
| 6,351,048 B1 | 2/2002 | Schob et al. |
| 6,355,998 B1 | 3/2002 | Schob et al. |
| 6,365,996 B2 | 4/2002 | Schob |
| 6,375,607 B1 | 4/2002 | Prem |
| 6,387,037 B1 | 5/2002 | Bolling et al. |
| 6,394,769 B1 | 5/2002 | Bearnson et al. |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,522,093 B1 | 2/2003 | Hsu et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,575,717 B2 | 6/2003 | Ozaki et al. |
| 6,589,030 B2 | 7/2003 | Ozaki |
| 6,595,762 B2 | 7/2003 | Khanwilkar et al. |
| 6,605,032 B2 | 8/2003 | Benkowski et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,641,378 B2 | 11/2003 | Davis et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,157 B2 | 4/2004 | Goldowsky |
| 6,716,189 B1 | 4/2004 | Jarvik et al. |
| 6,732,501 B2 | 5/2004 | Yu et al. |
| 6,749,598 B1 | 6/2004 | Keren et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,846,168 B2 | 1/2005 | Davis et al. |
| 6,860,713 B2 | 3/2005 | Hoover |
| 6,884,210 B2 | 4/2005 | Nose et al. |
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Beamson et al. |
| 6,966,748 B2 | 11/2005 | Woodard et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,048,681 B2 | 5/2006 | Tsubouchi et al. |
| 7,090,401 B2 | 8/2006 | Rahman et al. |
| 7,112,903 B1 | 9/2006 | Schob |
| 7,122,019 B1 | 10/2006 | Kesten et al. |
| 7,128,538 B2 * | 10/2006 | Tsubouchi et al. ............. 417/12 |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,202,582 B2 | 4/2007 | Eckert et al. |
| 7,241,257 B1 | 7/2007 | Ainsworth et al. |
| 7,284,956 B2 | 10/2007 | Nose et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,393,181 B2 | 7/2008 | McBride et al. |
| 7,431,688 B2 | 10/2008 | Wampler et al. |
| 7,462,019 B1 | 12/2008 | Allarie et al. |
| 7,467,930 B2 | 12/2008 | Ozaki et al. |
| 7,470,246 B2 | 12/2008 | Mori et al. |
| 7,476,077 B2 | 1/2009 | Woodard et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,660,635 B1 | 2/2010 | Verness et al. |
| 7,699,586 B2 | 4/2010 | LaRose et al. |
| 7,731,675 B2 | 6/2010 | Aboul-Hosn et al. |
| 7,748,964 B2 | 7/2010 | Yaegashi et al. |
| 7,802,966 B2 | 9/2010 | Wampler et al. |
| 7,841,976 B2 | 11/2010 | McBride et al. |
| 7,888,242 B2 | 2/2011 | Tanaka et al. |
| 7,934,909 B2 | 5/2011 | Nuesser et al. |
| 7,972,122 B2 | 7/2011 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,152,493 B2 | 4/2012 | LaRose et al. |
| 8,177,703 B2 | 5/2012 | Smith et al. |
| 8,226,373 B2 | 7/2012 | Yaehashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Akdis et al. |
| 8,535,211 B2 | 9/2013 | Campbell et al. |
| 8,585,290 B2 | 11/2013 | Bauer |
| 8,652,024 B1 | 2/2014 | Yanai et al. |
| 8,686,674 B2 | 4/2014 | Bi et al. |
| 8,770,945 B2 | 7/2014 | Ozaki et al. |
| 8,821,365 B2 | 9/2014 | Ozaki et al. |
| 8,827,661 B2 | 9/2014 | Mori |
| 8,864,644 B2 | 10/2014 | Yomtov |
| 8,968,174 B2 | 3/2015 | Yanai et al. |
| 9,067,005 B2 | 6/2015 | Ozaki et al. |
| 9,068,572 B2 | 6/2015 | Ozaki et al. |
| 9,109,601 B2 | 8/2015 | Mori |
| 9,132,215 B2 | 9/2015 | Ozaki et al. |
| 9,133,854 B2 | 9/2015 | Okawa et al. |
| 2001/0039369 A1 | 11/2001 | Terentiev |
| 2002/0051711 A1 | 5/2002 | Ozaki |
| 2002/0058994 A1 | 5/2002 | Hill et al. |
| 2002/0094281 A1 * | 7/2002 | Khanwilkar et al. ......... 417/356 |
| 2002/0095210 A1 | 7/2002 | Finnegan et al. |
| 2003/0023302 A1 | 1/2003 | Moe et al. |
| 2003/0045772 A1 | 3/2003 | Reich et al. |
| 2003/0072656 A1 | 4/2003 | Niwatsukino et al. |
| 2003/0144574 A1 | 7/2003 | Heilman et al. |
| 2003/0199727 A1 | 10/2003 | Burke |
| 2004/0007515 A1 | 1/2004 | Geyer |
| 2004/0015232 A1 | 1/2004 | Shu et al. |
| 2004/0024285 A1 | 2/2004 | Muckter |

(56) References Cited

U.S. PATENT DOCUMENTS

| | | |
|---|---|---|
| 2004/0030381 A1 | 2/2004 | Shu |
| 2004/0143151 A1 | 7/2004 | Mori et al. |
| 2004/0145337 A1 | 7/2004 | Morishita |
| 2004/0171905 A1 | 9/2004 | Yu et al. |
| 2004/0210305 A1 | 10/2004 | Shu et al. |
| 2004/0263341 A1 | 12/2004 | Enzinna |
| 2005/0008496 A1 | 1/2005 | Tsubouchi et al. |
| 2005/0025630 A1 | 2/2005 | Ayre et al. |
| 2005/0073273 A1 | 4/2005 | Maslov et al. |
| 2005/0089422 A1 | 4/2005 | Ozaki et al. |
| 2005/0131271 A1 | 6/2005 | Benkowski et al. |
| 2005/0141887 A1 | 6/2005 | Lelkes |
| 2005/0194851 A1 | 9/2005 | Eckert et al. |
| 2005/0261543 A1 | 11/2005 | Abe et al. |
| 2005/0287022 A1 | 12/2005 | Yaehashi et al. |
| 2006/0024182 A1 | 2/2006 | Akdis et al. |
| 2006/0055274 A1 | 3/2006 | Kim |
| 2006/0127227 A1 | 6/2006 | Mehlhorn et al. |
| 2007/0073393 A1 | 3/2007 | Kung et al. |
| 2007/0078293 A1 | 4/2007 | Shambaugh, Jr. |
| 2007/0114961 A1 | 5/2007 | Schwarzkopf |
| 2007/0134993 A1 | 6/2007 | Tamez et al. |
| 2007/0189648 A1 | 8/2007 | Kita et al. |
| 2007/0213690 A1 | 9/2007 | Phillips et al. |
| 2007/0231135 A1 | 10/2007 | Wampler et al. |
| 2007/0282298 A1 | 12/2007 | Mason |
| 2007/0297923 A1 | 12/2007 | Tada |
| 2008/0007196 A1 | 1/2008 | Tan et al. |
| 2008/0021394 A1 | 1/2008 | La Rose et al. |
| 2008/0030895 A1 | 2/2008 | Obara et al. |
| 2008/0095648 A1 | 4/2008 | Wampler et al. |
| 2008/0124231 A1 | 5/2008 | Yaegashi |
| 2008/0183287 A1 | 7/2008 | Ayre |
| 2008/0211439 A1 | 9/2008 | Yokota et al. |
| 2009/0041595 A1 | 2/2009 | Garzaniti et al. |
| 2009/0060743 A1 | 3/2009 | McBride et al. |
| 2009/0074336 A1 | 3/2009 | Engesser et al. |
| 2009/0171136 A1 | 7/2009 | Shambaugh, Jr. |
| 2009/0257693 A1 | 10/2009 | Aiello |
| 2010/0185280 A1 | 7/2010 | Ayre et al. |
| 2010/0222634 A1 | 9/2010 | Poirier |
| 2010/0256440 A1 | 10/2010 | Maher |
| 2010/0266423 A1 | 10/2010 | Gohean et al. |
| 2010/0305692 A1 | 12/2010 | Thomas et al. |
| 2011/0015732 A1 | 1/2011 | Kanebako |
| 2011/0112354 A1 | 5/2011 | Nishimura et al. |
| 2011/0118766 A1 | 5/2011 | Reichenbach et al. |
| 2011/0118829 A1 | 5/2011 | Hoarau et al. |
| 2011/0118833 A1 | 5/2011 | Reichenbach et al. |
| 2011/0129373 A1 | 6/2011 | Mori |
| 2011/0218383 A1 | 9/2011 | Broen et al. |
| 2011/0218384 A1 | 9/2011 | Bachman et al. |
| 2011/0218385 A1 | 9/2011 | Bolyare et al. |
| 2011/0243759 A1 | 10/2011 | Ozaki et al. |
| 2011/0318203 A1 | 12/2011 | Ozaki et al. |
| 2012/0003108 A1* | 1/2012 | Ozaki et al. ............... 417/413.1 |
| 2012/0016178 A1 | 1/2012 | Woodard et al. |
| 2012/0022645 A1 | 1/2012 | Burke |
| 2012/0035411 A1 | 2/2012 | LaRose et al. |
| 2012/0078030 A1 | 3/2012 | Bourque |
| 2012/0095281 A1 | 4/2012 | Reichenbach et al. |
| 2012/0130152 A1 | 5/2012 | Ozaki et al. |
| 2012/0226350 A1 | 9/2012 | Ruder et al. |
| 2012/0243759 A1 | 9/2012 | Fujisawa |
| 2012/0253103 A1 | 10/2012 | Robert |
| 2012/0308363 A1 | 12/2012 | Ozaki et al. |
| 2013/0121821 A1 | 5/2013 | Ozaki et al. |
| 2013/0158521 A1 | 6/2013 | Sobue |
| 2013/0170970 A1 | 7/2013 | Ozaki et al. |
| 2013/0178694 A1 | 7/2013 | Jeffery et al. |
| 2013/0243623 A1 | 9/2013 | Okawa et al. |
| 2013/0289334 A1 | 10/2013 | Badstibner et al. |
| 2014/0030122 A1 | 1/2014 | Ozaki et al. |
| 2014/0066690 A1 | 3/2014 | Siebenhaar et al. |
| 2014/0066691 A1 | 3/2014 | Siebenhaar |
| 2014/0200389 A1 | 7/2014 | Yanai et al. |
| 2014/0205467 A1 | 7/2014 | Yanai et al. |
| 2014/0275721 A1 | 9/2014 | Yanai et al. |
| 2014/0275727 A1 | 9/2014 | Bonde et al. |
| 2014/0296615 A1 | 10/2014 | Franano |
| 2014/0309481 A1 | 10/2014 | Medvedev et al. |
| 2014/0314597 A1 | 10/2014 | Allaire et al. |
| 2014/0323796 A1 | 10/2014 | Medvedev et al. |
| 2015/0017030 A1 | 1/2015 | Ozaki |
| 2015/0023803 A1 | 1/2015 | Fritz et al. |
| 2015/0078936 A1 | 3/2015 | Mori |
| 2015/0306290 A1 | 10/2015 | Rosenberg et al. |
| 2015/0374892 A1 | 12/2015 | Yanai et al. |
| 2016/0058929 A1 | 3/2016 | Medvedev et al. |
| 2016/0058930 A1 | 3/2016 | Medvedev et al. |

FOREIGN PATENT DOCUMENTS

| | | |
|---|---|---|
| CN | 102239334 A | 11/2011 |
| CN | 102341600 A | 2/2012 |
| EP | 2945662 B1 | 9/1999 |
| EP | 971212 A | 1/2000 |
| EP | 1113117 A2 | 7/2001 |
| EP | 1327455 A | 7/2003 |
| EP | 1430919 A1 | 6/2004 |
| EP | 1495773 A2 | 1/2005 |
| EP | 1598087 A2 | 3/2005 |
| EP | 1526286 A1 | 4/2005 |
| EP | 1495773 A3 | 11/2006 |
| EP | 1495773 B1 | 2/2009 |
| EP | 2292282 A1 | 3/2011 |
| EP | 2298375 A1 | 3/2011 |
| EP | 2372160 A1 | 10/2011 |
| EP | 2405140 A1 | 1/2012 |
| EP | 2405141 A1 | 1/2012 |
| EP | 2461465 A1 | 6/2012 |
| EP | 2538086 A1 | 12/2012 |
| EP | 2554191 A1 | 2/2013 |
| EP | 2594799 A1 | 5/2013 |
| EP | 2618001 A1 | 7/2013 |
| EP | 2693609 A1 | 2/2014 |
| EP | 2948202 A1 | 12/2015 |
| EP | 3013385 A2 | 5/2016 |
| JP | 58/9535 | 1/1983 |
| JP | 61/293146 | 12/1986 |
| JP | H02-033590 U | 3/1990 |
| JP | 04/091396 A | 3/1992 |
| JP | 04/148094 A | 5/1992 |
| JP | 05/021197 U | 3/1993 |
| JP | 06/014538 U | 2/1994 |
| JP | 06/053790 U | 7/1994 |
| JP | 2006/070476 | 9/1994 |
| JP | 2006/245455 | 9/1994 |
| JP | 07/014220 U | 3/1995 |
| JP | 07/042869 U | 8/1995 |
| JP | 07/509156 A | 10/1995 |
| JP | 09/122228 A | 5/1997 |
| JP | 10/331841 A | 12/1998 |
| JP | 11/244377 A | 9/1999 |
| JP | 2001/309628 | 11/2001 |
| JP | 2003/135592 A | 5/2003 |
| JP | 2004/166401 A | 6/2004 |
| JP | 2004/209240 A | 7/2004 |
| JP | 2004/332566 A | 11/2004 |
| JP | 2004/346925 A | 12/2004 |
| JP | 2005/94955 | 4/2005 |
| JP | 2005/127222 A | 5/2005 |
| JP | 2005/245138 | 9/2005 |
| JP | 2005/270345 A | 10/2005 |
| JP | 2005/270415 A | 10/2005 |
| JP | 2005/287599 A | 10/2005 |
| JP | 2006/167173 A | 6/2006 |
| JP | 2007/002885 A | 1/2007 |
| JP | 2007/043821 | 2/2007 |
| JP | 2007/089972 A | 4/2007 |
| JP | 2007/089974 | 4/2007 |
| JP | 2007/215292 | 8/2007 |
| JP | 2007/247489 | 9/2007 |
| JP | 2008/011611 | 1/2008 |

(56) References Cited

FOREIGN PATENT DOCUMENTS

| | | |
|---|---|---|
| JP | 2008/104278 | 5/2008 |
| JP | 2008/132131 | 6/2008 |
| JP | 2008/99453 | 8/2008 |
| JP | 2008/193838 | 8/2008 |
| JP | 2008/297997 A | 12/2008 |
| JP | 2008/301634 | 12/2008 |
| JP | 2006/254619 | 9/2009 |
| JP | 2010/133381 A | 6/2010 |
| JP | 2010/136863 A | 6/2010 |
| JP | 2010/203398 A | 9/2010 |
| JP | 2010/209691 A | 9/2010 |
| JP | 2011/169166 A | 9/2011 |
| JP | 2012/021413 | 2/2012 |
| JP | 2012/062790 A | 3/2012 |
| JP | 5171953 B2 | 3/2013 |
| JP | 5572832 B2 | 8/2014 |
| JP | 5656835 B2 | 1/2015 |
| WO | 93/07388 A1 | 4/1993 |
| WO | 94/14226 | 6/1994 |
| WO | 96/31934 | 10/1996 |
| WO | 97/42413 A1 | 11/1997 |
| WO | 00/64509 A1 | 11/2000 |
| WO | 2004/098677 A1 | 11/2004 |
| WO | 2005/011087 A1 | 2/2005 |
| WO | 2005/028000 A1 | 3/2005 |
| WO | 2005/034312 A2 | 4/2005 |
| WO | 2009/157408 A1 | 12/2009 |
| WO | 2010/067682 A1 | 6/2010 |
| WO | 2010/101082 A1 | 9/2010 |
| WO | 2010/101107 A1 | 9/2010 |
| WO | 2011/013483 A1 | 2/2011 |
| WO | 2012/040544 A1 | 3/2012 |
| WO | 2012/047550 A1 | 4/2012 |
| WO | 2012/132850 A1 | 10/2012 |
| WO | 2014/113533 A1 | 7/2014 |
| WO | 2014/116676 A1 | 7/2014 |
| WO | 2014/179271 A2 | 11/2014 |
| WO | 2016/033131 A1 | 3/2016 |
| WO | 2016/033133 A1 | 3/2016 |

OTHER PUBLICATIONS

International Search Report and Written Opinion issued in PCT/US2014/012511 mailed on May 14, 2014, 13 pp.

International Search Report and Written Opinion of PCT/US2014/017932 mailed on Jun. 16, 2014, 12 pages.

Asama, et al., "Suspension Performance of a Two-Axis Actively Regulated Consequent-Pole Bearingless Motor," IEEE Transactions on Energy Conversion, vol. 28, No. 4, Dec. 2013, 8 pages.

European Search report Issued in European Patent Application No. 10/748,702.7, mailed Apr. 2, 2013.

Extended European Search Report issued in European Patent Application No. EP 10748677.1, mailed Nov. 19, 2012.

International Search Report (PCT/ISA/210) issued on Jul. 14, 2009, by Japanese Patent Office as the International Searching Authority for International Application No. PCT/JP2009/061318.

International Search Report and Written Opinion issued in PCT/JP2011/050925, mailed Apr. 12, 2011.

International Search Report and Written Opinion issued in PCT/JP2011/054134, mailed Apr. 12, 2011.

International Search Report and Written Opinion issued in PCT/JP2011/064768, mailed Sep. 13, 2011.

International Search Report and Written Opinion issued in PCT/JP2011/070450, mailed Dec. 13, 2011.

Kosaka, et al.,"Operating Point Control System for a Continuous Flow Artificial Heart: In Vitro Study," ASAIO Journal 2003, 6 pages.

Supplementary European Search Report issued in European Application No. 09/831,788.6, dated Jan. 7, 2013, 7 pages.

Terumo Heart, Inc., "Handled With Care—Significantly Reduce the Risk of Cell Damage," Terumo brochure, Apr. 2010, 2 pages.

Yamazaki, et al., "Development of a Miniature Intraventricular Axial Flow Blood Pump," ASAIO Journal, 1993, 7 pages.

Asama, J., et al., "A Compact Highly Efficient and Low Hemolytic Centrifugal Blood Pump With a Magnetically Levitated Impeller", Artificial Organs, vol. 30, No. 3, Mar. 1, 2006 (Mar. 1, 2006), pp. 160-167.

Asama, J., et al., "A New Design for a Compact Centrifugal Blood Pump with a Magnetically Levitated Rotor", Asaio Journal, vol. 50, No. 6, Nov. 1, 2004 (Nov. 1, 2004), pp. 550-556.

Extended European Search Report issued on Mar. 26, 2015 in European Patent Application No. EP 09770118.9, filed Jun. 22, 2009, all pages.

European office action mailed on Jan. 27, 2016 for EP 10804230.0, all pages.

Extended European Search Report issued in European Patent Application No. EP 11806627.3, mailed Oct. 8, 2014, all pages.

Extended European Search Report issued in European Patent Application No. EP 11825062, mailed Jun. 18, 2015, all pages.

Extended European Search Report mailed on Feb. 4, 2016 in European Patent Application No. EP 12764433.4, filed Mar. 12, 2012, all pages.

International Search Report and Written Opinion of PCT/US2014/011786, mailed on May 5, 2014, all pages.

International Preliminary Report on Patentability mailed on Jul. 30, 2015 for International Patent Application No. PCT/US2014/011786, filed on Jan. 16, 2014, all pages.

International Search Report and Written Opinion of PCT/US2014/012511, mailed on May 147, 2014, all pages.

International Preliminary Report on Patentability mailed on Aug. 6, 2015 for International Patent Application No. PCT/US2014/012511, filed on Jan. 22, 2014, all pages.

International Search Report and Written Opinion of PCT/US2014/012502, dated May 9, 2014, all pages.

International Preliminary Report on Patentability mailed on Aug. 6, 2015 for International Patent Application No. PCT/US2014/012502, filed on Jan. 22, 2014, all pages.

International Search Report and Written Opinion of PCT/US2014/017932, mailed on Jun. 16, 2014, all pages.

International Preliminary Report on Patentability mailed on Sep. 11, 2015 for International Patent Application No. PCT/US2014/017932, filed on Feb. 24, 2014, all pages.

International Search Report and Written Opinion of PCT/US2014/035798, mailed on Feb. 11, 2016, all pages.

International Preliminary Report on Patentability issued Feb. 16, 2016 for International Patent Application No. PCT/US2014/035798, filed on Apr. 29, 2014, all pages.

International Search Report and Written Opinion of PCT/US2016/017611, mailed on May 16, 2016, all pages.

International Search Report and Written Opinion of PCT/US2016/017791, mailed on May 16, 2016, all pages.

Japanese office action mailed on Dec. 8, 2015 JP 2013-507344, all pages.

Decision to Grant for JP 2013-507344 issued Jun. 14, 2016, all pages.

Neethu, S., et al., "Novel design, optimization and realization of axial flux motor for implantable blood pump", Power Electronics, Drives and Energy Systems (PEDES) & 2010 Power Indian, 2010 Joint International Conference on, IEEE, Dec. 20, 2010 (Dec. 20, 2010), pp. 1-6.

Sandtner, J., et al., "Electrodynamic Passive Magnetic Bearing with Planar Halbach Arrays", Aug. 6, 2004 (Aug. 6, 2004), retrieved from the internet: <http://www.silphenix.ch/lexington.pdf>, all pages.

International Search Report and Written Opinion of PCT/US2016/017812, mailed on Jun. 7, 2016, all pages.

International Search Report and Written Opinion of PCT/US2016/017864, mailed Jun. 8, 2016, all pages.

* cited by examiner

STARTUP SEQUENCE FOR CENTRIFUGAL PUMP WITH LEVITATED IMPELLER

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to centrifugal pumping devices for circulatory assist and other uses, and, more specifically, to an improved startup of a magnetically-levitated impeller that avoids excessive wear of the impeller against the housing before levitation is obtained.

Many types of circulatory assist devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. One such system is the DuraHeart® LVAS system made by Terumo Heart, Inc., of Ann Arbor, Mich. The DuraHeart® system employs a centrifugal pump with a magnetically levitated impeller to pump blood from the left ventricle to the aorta. The impeller acts as a rotor of an electric motor in which a rotating magnetic field from a multiphase stator couples with the impeller and is rotated at a speed appropriate to obtain the desired blood flow through the pump.

A control system for varying pump speed to achieve a target blood flow based on physiologic conditions is shown in U.S. Pat. No. 7,160,243, issued Jan. 9, 2007, which is incorporated herein by reference in its entirety. The stator of the pump motor can be driven by a pulse-width modulated signal determined using a field-oriented control (FOC) as disclosed in U.S. application Ser. No. 13/748,780, filed Jan. 24, 2013, entitled "Impeller Position Compensation Using Field Oriented Control," which is incorporated herein by reference in its entirety.

The centrifugal pump employs a sealed pumping chamber. By levitating the impeller within the chamber when it rotates, turbulence in the blood is minimized. The spacing between the impeller and chamber walls minimizes pump-induced hemolysis and thrombus formation. The levitation is obtained by the combination of a magnetic bearing and a hydrodynamic bearing. For the magnetic bearing, the impeller typically employs upper and lower plates having permanent magnetic materials for interacting with a magnetic field applied via the chamber walls. For example, a stationary magnetic field may be applied from the upper side of the pump housing to attract the upper plate while a rotating magnetic field from the lower side of the pump housing (to drive the impeller rotation) attracts the lower plate. The hydrodynamic bearing results from the action of the fluid between the impeller and the chamber walls while pumping occurs. Grooves may be placed in the chamber walls to enhance the hydrodynamic bearing (as shown in U.S. Pat. No. 7,470,246, issued Dec. 30, 2008, titled "Centrifugal Blood Pump Apparatus," which is incorporated herein by reference). The magnetic and hydrodynamic forces cooperate so that the impeller rotates at a levitated position within the pumping chamber. Since the hydrodynamic forces change according to the rotation speed of the impeller, the magnetic field may be actively controlled in order to ensure that the impeller maintains a centered position with the pumping chamber.

Prior to starting rotation of the impeller, the axial forces acting on it are not balanced. Magnetic attraction causes the impeller to rest against one of the upper or lower chamber walls. In many pump designs, it is possible for the impeller to be arbitrarily resting against either one of the walls. When rotation begins, the rubbing of the impeller against the chamber wall can cause undesirable mechanical wear of the impeller and/or wall. The amount of wear is proportional to the rotation angle traversed until the impeller lifts off of the pump housing and to the normal force between the impeller and housing.

In a typical startup sequence of the prior art, the stator coils are energized to produce a strong, stationary magnetic field that rotates the impeller into alignment with a known phase angle. When the impeller moves during alignment, it typically overshoots the desired position due to the strong field and then it oscillates around the desired position until the motion dampens out. Much mechanical wear can occur during this step. Once in the aligned position, the field-oriented control can begin closed-loop control to accelerate the impeller until the bearing forces separate it from the chamber wall. However, the normal force can be high before separation occurs, further increasing the wear.

SUMMARY OF THE INVENTION

In one aspect of the invention, a centrifugal pump system comprises a disc-shaped impeller rotating about an axis and having a first magnetic structure disposed at a first surface and a second magnetic structure disposed at a second surface. A pump housing defines a pumping chamber which receives the impeller. A levitation magnetic structure is disposed at a first end of the pump housing having a levitating magnetic field for axially attracting the first magnetic structure. A multiphase magnetic stator is disposed at a second end of the pump housing for generating a rotating magnetic field for axially and rotationally attracting the second magnetic structure. A commutator circuit provides a plurality of phase voltages to the stator. A sensing circuit determines respective phase currents flowing in response to the phase voltages. A controller calculates successive commanded values for the phase voltages during a running state in response to a desired impeller speed and an actual impeller phase that is detected in response to the determined phase currents. The controller has a startup interval during which the commanded values of the phase voltages are determined in response to a pseudo impeller phase and in response to a ramping gain factor.

DETAILED DESCRIPTION OF PREFERRED EMBODIMENTS

Figure 1:
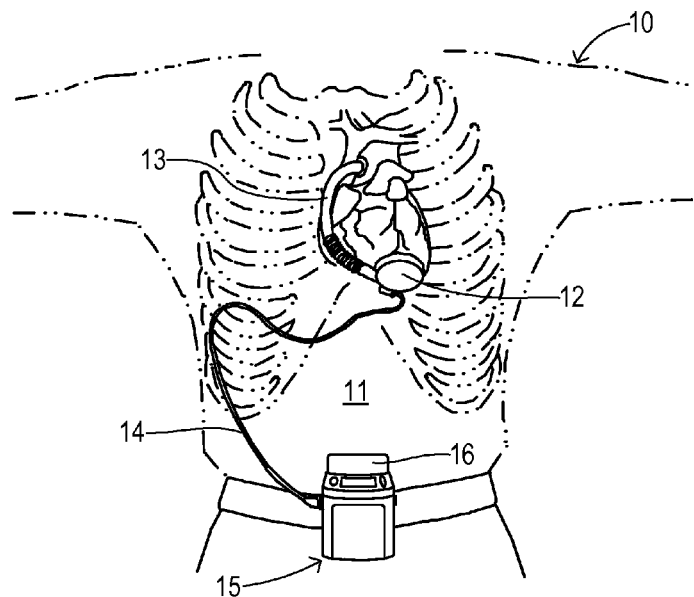
FIG. 1 is a diagram of a circulatory assist system as one example of an implantable pump employing the present invention.

Referring to FIG. 1, a patient 10 is shown in fragmentary front elevational view. Surgically implanted either into the patient's abdominal cavity or pericardium 11 is the pumping unit 12 of a ventricular assist device. An inflow conduit (on the hidden side of unit 12) pierces the heart to convey blood from the patient's left ventricle into pumping unit 12. An outflow conduit 13 conveys blood from pumping unit 12 to the patient's aorta. A percutaneous power cable 14 extends from pumping unit 12 outwardly of the patient's body via an incision to a compact control unit 15 worn by patient 10. Control unit 15 is powered by a main battery pack 16 and/or an external AC power supply and an internal backup battery. Control unit 15 includes a commutator circuit for driving a motor stator within pumping unit 12.

Figure 2:
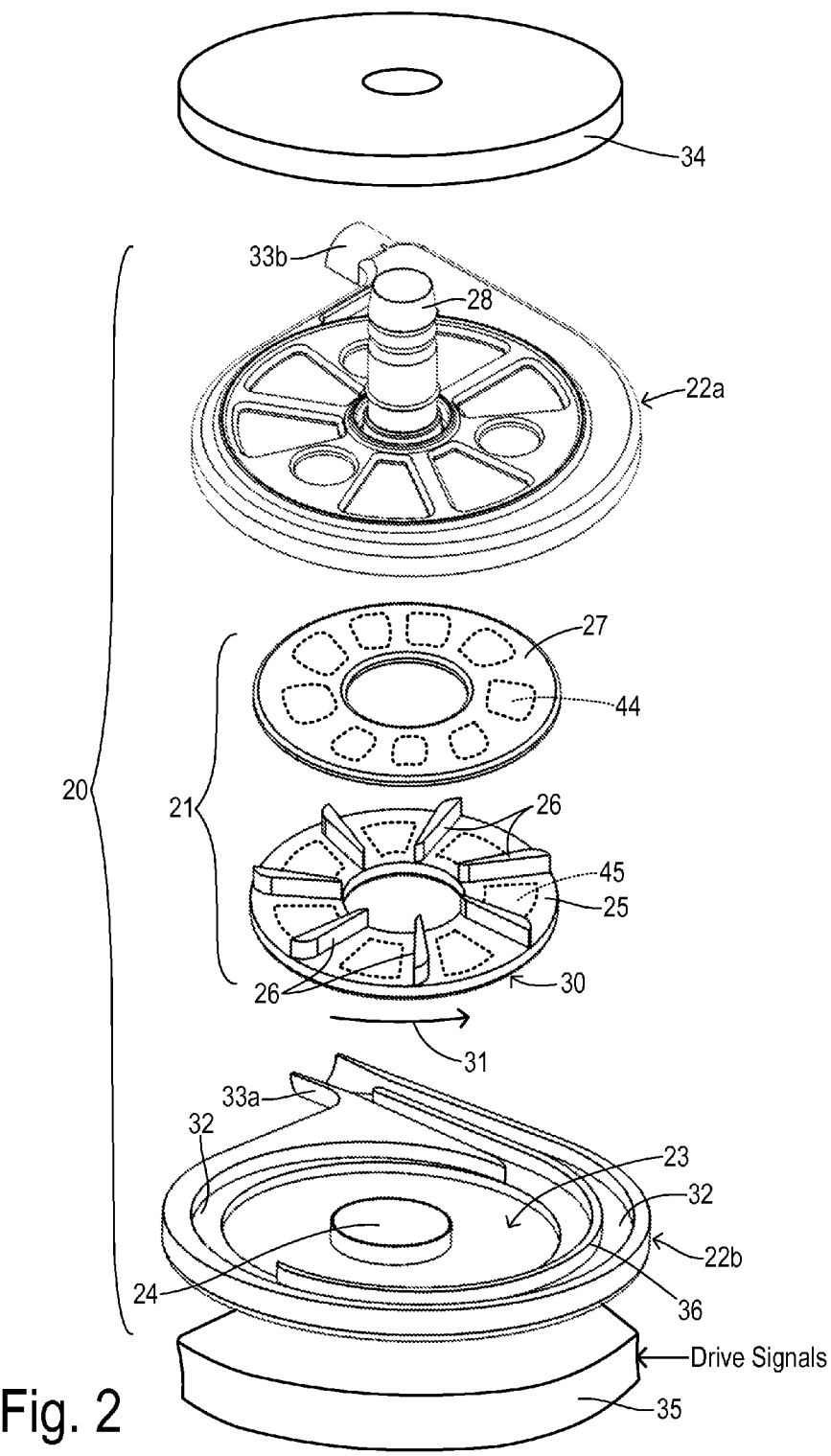
FIG. 2 is an exploded, perspective view of a centrifugal pump.

FIG. 2 shows a centrifugal pump unit 20 having an impeller 21 and a pump housing having upper and lower halves 22a and 22b. Impeller 21 is disposed within a pumping chamber 23 over a hub 24. Impeller 21 includes a first plate or disc 25 and a second plate or disc 27 sandwiched over a plurality of vanes 26. Second disc 27 includes a plurality of embedded magnet segments 44 for interacting with a levitating magnetic field created by levitation magnet structure 34 disposed against housing 22a. For achieving a small size, magnet structure 34 preferably is comprised of one or more permanent magnet segments providing a symmetrical, static levitation magnetic field around a 360° circumference. First disc 25 also contains embedded magnet segments 45 for magnetically coupling with a magnetic field from a stator assembly 35 disposed against housing 22b. Housing 22a includes an inlet 28 for receiving blood from a patient's ventricle and distributing it to vanes 26. Impeller 21 is preferably circular and has an outer circumferential edge 30. By rotatably driving impeller 21 in a pumping direction 31, the blood received at an inner edge of impeller 21 is carried to outer circumferential 30 and enters a volute region 32 within pumping chamber 23 at an increased pressure. The pressurized blood flows out from an outlet 33 formed by housing features 33a and 33b. A flow-dividing guide wall 36 may be provided within volute region 32 to help stabilize the overall flow and the forces acting on impeller 21.

Figure 3:
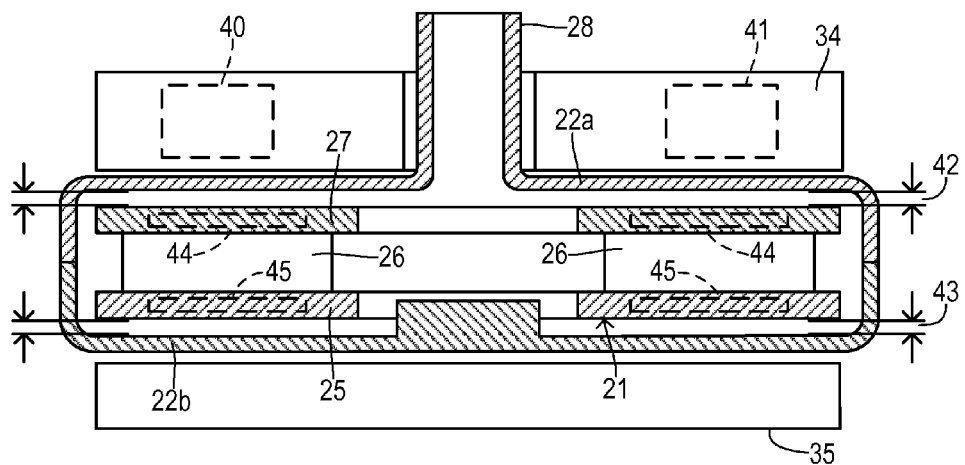
FIG. 3 is a cross section showing an impeller levitated to a centered position within a pumping chamber.

The cross section of FIG. 3 shows impeller 21 located at a centered position wherein disc 27 is spaced from housing 22A by a gap 42 and impeller disc 25 is spaced from housing 22B by a gap 43. During pump operation, the center position is maintained by the interaction of attractive magnetic forces between permanent magnets 40 and 41 in levitation magnet structure 34 with imbedded magnetic material 44 within impeller disc 27, and between stator assembly 35 and imbedded magnet material 45 in impeller disc 25, and by hydrodynamic bearing forces exerted by the circulating fluid which may be increased by forming hydrodynamic pressure grooves in housing 22 (not shown). By using permanent magnets in structure 34, a compact shape is realized and potential failures associated with the complexities of implementing active levitation magnet control are avoided. The present invention is equally applicable to other magnetic levitation structures with or without active control.

Figure 4:
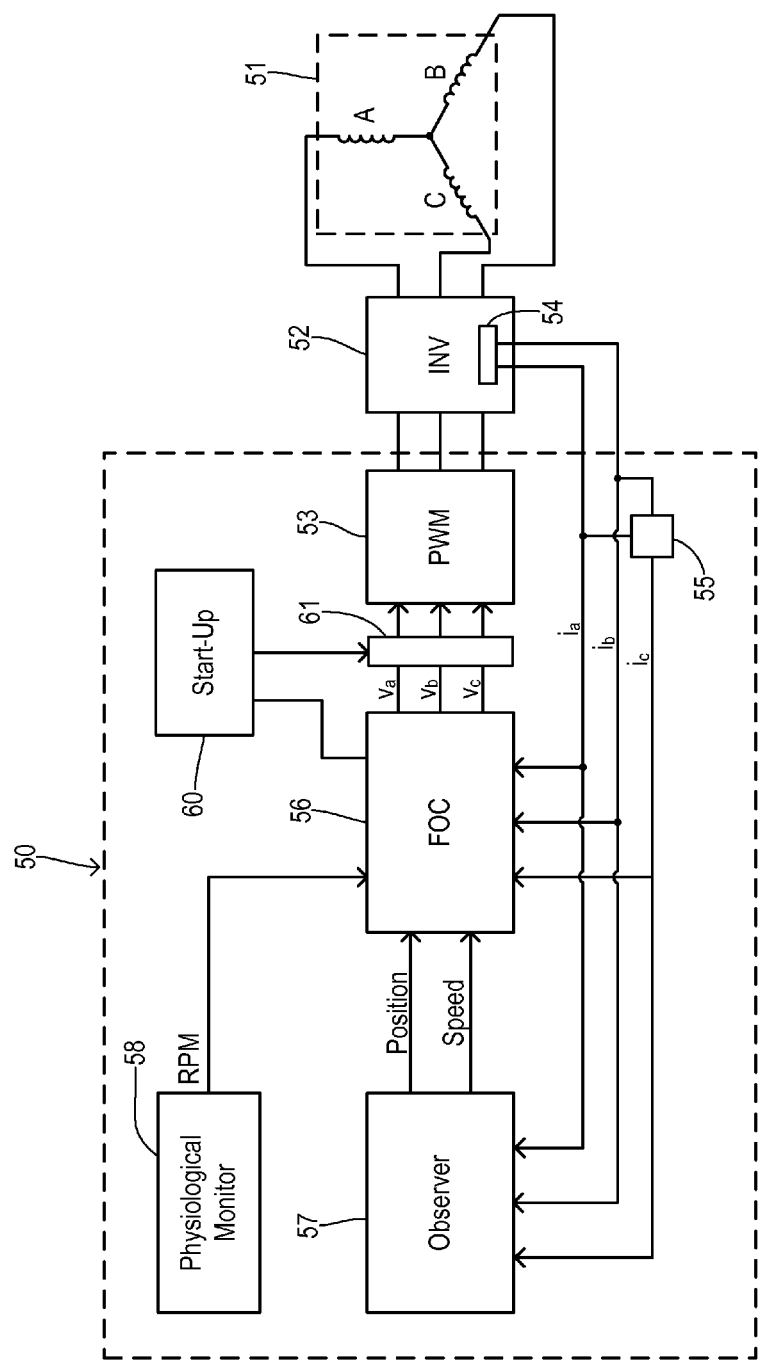
FIG. 4 is a block diagram showing multiphase stator windings and a control system according to the present invention.

A typical method for controlling voltages applied to a stator in order to provide the desired rotation for a permanent magnet rotor (i.e., the impeller) is a field-oriented control (FOC) algorithm, which is also known as vector control. FIG. 4 shows an FOC-based controller 50 which supplies a multiphase voltage signal to a three-phase stator assembly 51. Individual phases A, B, and C are driven by an H-bridge inverter 52 functioning as a commutation circuit driven by a pulse width modulator (PWM) circuit 53 in controller 50. A current sensing circuit 54 associated with inverter 52 measures instantaneous phase current in at least two phases providing current signals designated $i_a$ and $i_b$. A current calculating block 55 receives the two measured currents and calculates a current $i_c$ corresponding to the third phase as known in the art. The measured currents are input to an FOC block 56 and to a current observer block 57. Block 57 estimates the position and speed of the impeller as known in the art. The impeller position and speed are input to FOC block 56. A target speed or rpm for operating the pump is provided by a conventional physiological monitor 58 to FOC block 56. The target rpm may be set by a medical caregiver or determined according to an algorithm based on various patient parameters such as heart beat.

FOC block 56 generates commanded voltage output values $v_a$, $v_b$, and $v_c$ which are coupled to PWM block 53 via a startup filter 61 which is controlled by a startup logic block 60. In a normal running state, voltage commands $v_a$, $v_b$, and $v_c$ are unmodified by filter 61. During a startup interval, startup logic 60 alters the operation of FOC block 56 by generating a pseudo impeller position (i.e., phase) for use by the FOC algorithm and by directly modifying the generated values for $v_a$, $v_b$, and $v_c$ according to a gradually increasing gain factor.

When the impeller is not rotating under field oriented control, current observer block 57 is unable to estimate the actual position (i.e., the phase angle) of the impeller. For that reason, it is common in the prior art to generate a large, stationary magnetic field pulse from the stator in order to force the impeller into a known position. Based on the known position and an initial impeller speed of zero, the prior art controller was able to accelerate the impeller in a controlled (i.e., closed-loop) fashion. The large, stationary magnetic field pulse is not a problem for a radial type of motor structure or for a motor with a mechanical shaft and bearings. However, in the mechanical-bearingless (i.e., levitating) axial motor drive system for a blood pump, the alignment step is not desirable because the large, stationary magnetic field pulse may create oscillation movement of the impeller as a spring/mass system, and it may increase the normal force between the impeller and pump housing as a result of the large magnetic field. The oscillating movement and increased normal force may induce mechanical damage to the pump housing surface. The roughened blood pump surface may promote blood clot which is one of the severe failure modes of this type of device. In order to avoid the alignment step, the present invention adopts a gradual ramping up of voltage commands as the stator magnetic field is rotated using an arbitrary (i.e., pseudo) phase. The gradually increasing magnetic field will eventually catch the impeller to achieve a rotation that eventually becomes sufficiently locked in to enable observer 57 to detect the actual phase and speed of the impeller. Once the impeller is caught by the magnetic field and starts to rotate, the impeller will be suspended by hydrodynamic forces, and no mechanical wear will happen. Due to the gradually increasing magnetic field, the impeller is not very likely to be pulled in a backwards direction (in part because no movement can be generated until the rotating magnetic field overcomes the static friction between the impeller and pump housing). In addition, the speed of rotation of the magnetic field can be performed with a gradual acceleration to improve the likelihood of "catching" the impeller and rotating it in the desired direction. In the event that the ramping sequence fails to catch the impeller, observer 57 will detect that a valid position has not yet been determined. If no valid impeller position has been detected by observer 57 within a predetermined time, the ongoing startup attempt can be terminated and a second attempt can be made to start the impeller.

More specifically, startup logic block 60 may provide a pseudo impeller phase to FOC block 56, wherein the pseudo phase of the impeller has a chosen initial value and then follows a gradually accelerating rotation rate (not to exceed a target rotation speed).

Figure 5:
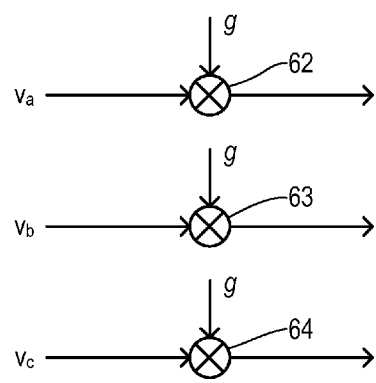
FIG. 5 represents a gain function for ramping up the phase voltage commands during startup.

As shown in FIG. 5, filter 61 may provide a variable gain g multiplied separately by each voltage command v in order to gradually ramp up the magnitude of the rotating magnetic field over a certain period of time. As impeller rotation begins, this generates a gradually increasing torque applied to the impeller and a gradual increase in the normal force between the impeller and pump housing. A set of multipliers 62-64 each receives the gain factor g at its first input and each receives a respective voltage command $v_a$-$v_c$ at its second input. In a normal running state of the pump, gain factor g is equal to one. During a startup interval, gain factor g provides a gradually increasing profile such as shown in FIG. 6 or 7.

Figure 6:
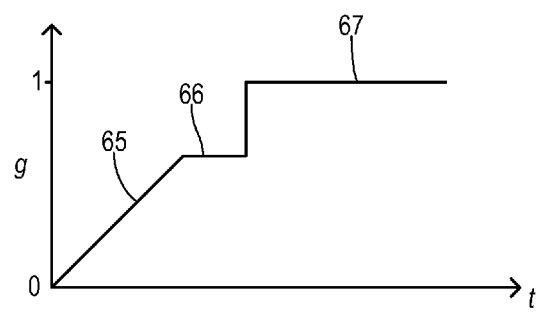
FIG. 6 shows one embodiment of a ramping gain during a successful startup of the pump.

In FIG. 6, gain g starts at zero and then increases along a segment 65 with a predetermined slope. Once gain g reaches a predetermined magnitude at 66 which is less than 1, the ramping ceases. The magnetic field continues to rotate for a predetermined time which is chosen to be long enough to allow the current observer to converge on a valid estimate of the impeller phase and speed if the impeller has been properly "caught" by the rotating magnetic field. If a valid estimate is detected, then gain factor g preferably increases to its full value (e.g., 1) at 67 and then the normal running state commences.

Figure 7:
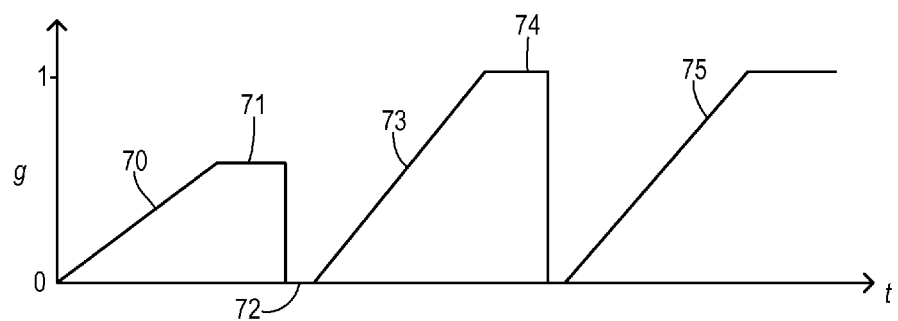
FIG. 7 illustrates a ramping gain for repeated startup attempts.

FIG. 7 illustrates a sequence wherein a first open-loop attempt to start the impeller rotation (i.e., using a pseudo impeller phase and an accelerating rotation rate while ramping the phase voltage commands) fails to establish the desired rotation that is necessary for the current observer to converge on a valid estimate of the actual impeller phase. Thus, gain factor g is ramped from zero up to a predetermined gain along slope 70 and maintains the constant value at 71. When the current observer does not indicate that a valid estimate for the actual impeller phase has been obtained, then the starting attempt is halted and the stator magnetic field may be turned off at 72. After a time delay to ensure that the impeller is stationary, gain factor g is again ramped upward from zero along segment 73 and is then kept at a maximum value (e.g., 1) at 74 for a predetermined time. In the second attempt at starting the impeller, the success of the startup represent a higher priority than the mechanical wear. Consequently, both the slope at 73 and the maximum gain at 74 may be greater than they were during the first attempt at 70 and 71. In the unlikely event that the second attempt likewise fails to achieve a startup (as identified by the current observer converging to a valid estimate for the actual impeller phase), a third attempt may be made to start the impeller at segment 75. Once one of the attempts has successfully started the impeller rotation, then gain factor g remains at a value of 1 for as long as the normal running state continues.

Figure 8:
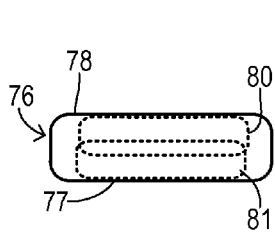
FIG. 8 shows an impeller in the pump housing having a random position prior to startup.
Figure 9:
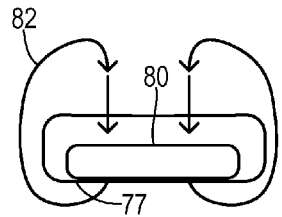
FIG. 9 shows the magnetic positioning of the impeller onto a predetermined side of the pump housing.
Figure 10:
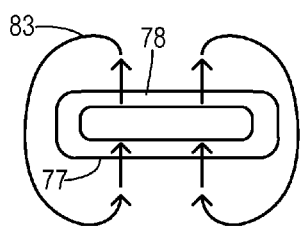
FIG. 10 shows a magnetic reversal for pushing the impeller from the predetermined side of the pump housing toward the other side in order to achieve liftoff at the time that rotation is started.

In combination with, or used separately from, the ramping up magnetic field and accelerating rotation rate, the present invention may employ an axial transport maneuver before beginning rotation of the magnetic field in order to lift off the impeller from the pump housing in order to avoid all normal forces during the initial rotation. As shown in FIG. 8, the pumping chamber in a pump housing 76 has a first end 77 and a second end 78 for retaining an impeller. The impeller may initially be retained in a position 81 against end 77 or a position 80 against end 78. Due to the permanent magnets in the impeller, when in a rest state the impeller will always be attracted to one end or the other of the pump housing. The axial transport maneuver involves generating the stator magnetic field to shift the impeller position from one end toward the other so that the rotation can be initiated while the impeller is moving between the ends, but first the impeller must be set to a known position. Thus, an external magnetic field 82 is generated as shown in FIG. 9 to place the impeller against a predetermined one of the ends such as end 77. By magnetically attracting the impeller to a known position 80, then it becomes possible to reverse the magnetic field as shown at 83 in FIG. 10 to propel the impeller between the ends of the pump housing, making it pass through a central levitated position. By controlling the magnitude and slope of the reversed polarity magnetic field, the resulting axial movement of the impeller is slow enough that the desired impeller rotation can be initiated before the impeller reaches the other end of the housing.

Figure 11:
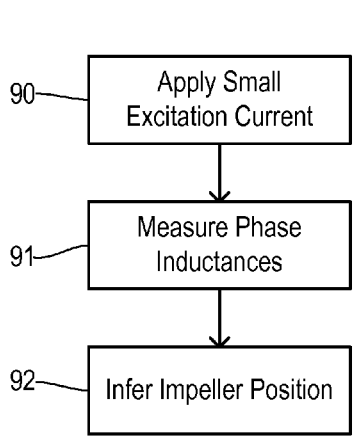
FIG. 11 shows an initial random phase position of the impeller prior to startup.
Figure 12:
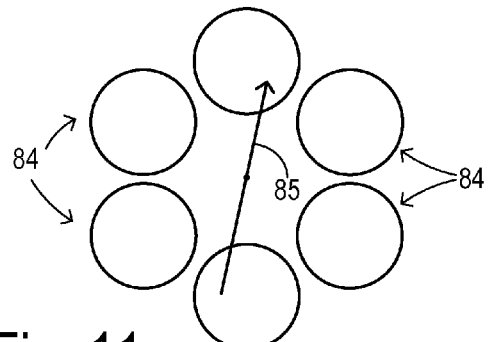
FIG. 12 is a flowchart showing a method for measuring the initial phase of the impeller.

In order to ensure that the impeller is attracted and then repulsed as desired, it is preferable to discover the actual impeller phase angle so that an appropriate energization of the stator can be determined that will provide the desired attraction and repulsion of the impeller. As shown in FIG. 11, the plurality of stator windings 84 are laid out at respective phases around the circumference of the pump housing, while an actual impeller phase 85 initially has some arbitrary orientation. The presence of impeller influences the inductance of each stator coil by an amount that depends on the actual phase of the impeller. Thus, by characterizing the relative inductance between different stator coils, the phase of the impeller can be inferred without requiring any movement of the impeller. As shown in FIG. 12, a small excitation current is applied to each phase of the stator in step 90. The inductance of each stator phase is measured in step 91. In step 92, the impeller position is inferred from the measured phase inductances. For example, a table can be generated in advance based on repeatedly 5 measuring all the phase inductances with the impeller placed at different phase angles and then storing the measurement results in a table for later comparison with the actual measured inductances to determine the initial impeller phase for conducting the startup interval. Besides being used to initiate the axial transport maneuver, the estimated impeller phase can be used as an initial value for the pseudo impeller phase used during rotation of the magnetic field during the startup interval as described above, which will further increase the likelihood of obtaining a valid startup of the pump on the first attempt.

Figure 13:
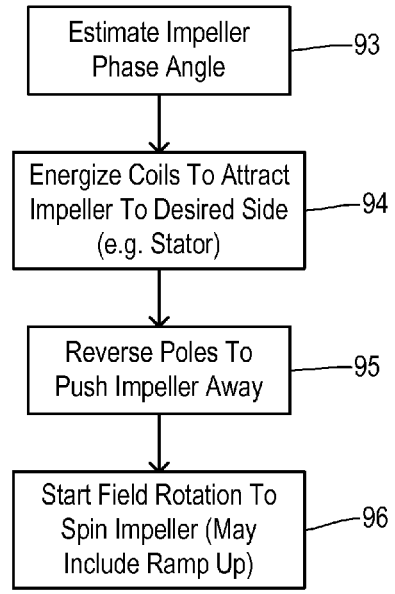
FIG. 13 is a flowchart showing one preferred method for axially transporting the impeller off the pump housing and then initiating impeller rotation.

FIG. 13 shows a preferred method for the axial transport maneuver wherein the impeller phase angle is estimated in step 93 as described above. Based on the estimated phase angle, the stator coils are energized in step 94 to attract the impeller to a predetermined end of the pump housing, e.g., the stator side of the housing. In step 95, the magnetic poles are reversed in order to push the impeller away from the predetermined end of the pump housing. While the impeller is moving between the ends, the magnetic field rotation is started in step 96 to begin to spin the impeller. When rotation of the magnetic field starts, the field oriented control is operated in an open-loop mode using a pseudo impeller phase which rotates with an increasing angular speed as described above. Preferably, the initial pseudo impeller phase uses a value determined from step 93. Preferably, the magnetic field rotation may include the use of the ramping gain factor, but that may not be required if the impeller phase angle is accurately estimated.

Although the present invention is especially useful in a centrifugal pump with a levitated impeller for pumping blood in cardiac assist applications, it is also applicable to other types of centrifugal pumps and for other applications.

What is claimed is:

1. A centrifugal pump system comprising:
  a disc-shaped impeller rotating about an axis and having a first magnetic structure disposed at a first surface and a second magnetic structure disposed at a second surface;
  a pump housing defining a pumping chamber which receives the impeller;
  a levitation magnetic structure disposed at a first end of the pump housing having a levitating magnetic field for axially attracting the first magnetic structure;
  a multiphase magnetic stator disposed at a second end of the pump housing for generating a rotating magnetic field for axially and rotationally attracting the second magnetic structure;
  a commutator circuit for providing a plurality of phase voltages to the stator;
  a sensing circuit determining respective phase currents flowing in response to the phase voltages; and
  a controller calculating successive commanded values for the phase voltages during a running state in response to a desired impeller speed and an angular position of the impeller that is detected in response to the determined phase currents, wherein the controller has a startup interval during which the commanded values of the phase voltages are determined in response to the angular position of the impeller and a ramping gain factor.

2. The system of claim 1 wherein the angular position of the impeller has a predetermined acceleration coinciding with the ramping gain factor.

3. The system of claim 1 further comprising:
  a current observer receiving the respective phase currents to estimate the angular position of the impeller, wherein the current observer generates a validation message when the determined phase currents have been sufficient to enable the current observer to generate a valid estimate;
  wherein the validation message is received by the controller which switches from the startup interval to the running state.

4. The system of claim 3 wherein if the controller does not receive the validation message within a predetermined period, then the ramping of the gain factor is repeated with a faster slope.

5. The system of claim 1 wherein the angular position of the impeller has an initial value estimated in response to relative inductances of respective phase windings of the stator.

6. The system of claim 1 wherein the angular position of the impeller has an initial value estimated in response to relative inductances of respective phase windings of the stator, and wherein the startup interval includes an axial transport maneuver before generating the successive commanded values;
  wherein the axial transport maneuver is comprised of magnetically attracting the impeller to a predetermined one of the first and second ends of the pump housing, and then magnetically propelling the impeller from the predetermined one of the ends to the other of the first and second ends; and
  wherein the successive commanded values begin so that the impeller begins to rotate while the impeller is being propelled between the ends of the pump housing.

7. A centrifugal pump system comprising:
  a disc-shaped impeller rotating about an axis and having a first magnetic structure disposed at a first surface and a second magnetic structure disposed at a second surface;
  a pump housing defining a pumping chamber which receives the impeller;
  a levitation magnetic structure disposed at a first end of the pump housing having a levitating magnetic field for axially attracting the first magnetic structure;
  a multiphase magnetic stator disposed at a second end of the pump housing for generating a rotating magnetic field for axially and rotationally attracting the second magnetic structure;
  a commutator circuit for providing a plurality of phase voltages to the stator;
  a sensing circuit determining respective phase currents flowing in response to the phase voltages; and
  a controller calculating successive commanded values for the phase voltages during a running state in response to a desired speed and an angular position of the impeller that is detected in response to the determined phase currents, wherein the controller has a startup interval including an axial transport maneuver before generating the successive commanded values;
  wherein the axial transport maneuver is comprised of magnetically attracting the impeller to a predetermined one of the first and second ends of the pump housing, and then magnetically propelling the impeller from the predetermined one of the ends of the pump housing to the other of the ends; and
  wherein the successive commanded values begin so that the impeller begins to rotate while the impeller is being propelled between the ends of the pump housing.

8. A cardiac assist device for implanting in a patient, comprising:
  a disc-shaped impeller rotating about an axis and having a first magnetic structure disposed at a first surface and a second magnetic structure disposed at a second surface;

a pump housing defining a pumping chamber which receives the impeller, wherein the pump housing includes an inlet for receiving blood from a heart of the patient and an outlet for delivering blood to a circulatory vessel of the patient;

a levitation magnetic structure disposed at a first end of the pump housing having a levitating magnetic field for axially attracting the first magnetic structure;

a multiphase magnetic stator disposed at a second end of the pump housing for generating a rotating magnetic field for axially and rotationally attracting the second magnetic structure;

a commutator circuit for providing a plurality of phase voltages to the stator;

a sensing circuit determining respective phase currents flowing in response to the phase voltages; and a controller calculating successive commanded values for the phase voltages during a running state in response to a desired speed and an angular position of the impeller that is detected in response to the determined phase currents, wherein the controller has a startup interval during which the commanded values of the phase voltages are determined in response to the angular position of the impeller and a ramping gain factor.

9. A method of operating a centrifugal pump having an impeller rotating suspended within a pumping chamber of a pump housing, comprising the steps of:
providing a first magnetic structure disposed at a first surface of the impeller and a second magnetic structure disposed at a second surface of the impeller;
providing a levitating magnetic field from a first end of the pump housing for axially attracting the first magnetic structure;
providing a multiphase magnetic stator disposed at a second end of the pump housing for generating a rotating magnetic field for axially and rotationally attracting the second magnetic structure;
supplying a plurality of phase voltages to the stator from an electrical commutator;
determining respective phase currents flowing in response to the phase voltages;
calculating successive commanded values for the phase voltages during a startup interval according to an angular position of the impeller and in response to a ramping gain factor; and
calculating successive commanded values for the phase voltages during a running state of the pump in response to a desired impeller speed and the angular position of the impeller that is detected in response to the determined phase currents.

10. The method of claim 9 wherein the angular position of the impeller has a predetermined acceleration coinciding with the ramping gain factor.

11. The method of claim 9 further comprising the steps of:
a current observer estimating the angular position of the impeller in response to the respective phase currents, wherein the current observer generates a validation message when the determined phase currents have been sufficient to enable the current observer to generate a valid estimate; and
the controller switching from the startup interval to the running state at a time after the validation message in generated.

12. The method of claim 11 further comprising the step of:
repeating the ramping of the gain factor with a faster slope if the validation message is not generated within a predetermined period.

13. The method of claim 9 further comprising the step of estimating an initial value of the angular position of the impeller in response to relative inductances of respective phase windings of the stator.

14. The method of claim 9 further comprising the steps of:
estimating an initial value of the angular position of the impeller in response to relative inductances of respective phase windings of the stator;
performing an axial transport maneuver before generating the successive commanded values comprised of magnetically attracting the impeller to a predetermined one of the first and second ends of the pump housing, and then magnetically propelling the impeller from the predetermined one of the ends to the other of the first and second ends;
wherein the successive commanded values begin so that the angular position of the impeller begins to rotate while the impeller is being propelled between the ends of the pump housing.

15. A centrifugal pump system comprising:
a disc-shaped impeller for rotating about an axis and having a first magnetic structure disposed at a first surface and a second magnetic structure disposed at a second surface;
a pump housing defining a pumping chamber which receives the impeller;
a levitation magnetic structure disposed at a first end of the pump housing having a levitating magnetic field for axially attracting the first magnetic structure;
a multiphase magnetic stator disposed at a second end of the pump housing for generating a rotating magnetic field for axially and rotationally attracting the second magnetic structure; and
a controller configured to:
cause a plurality of phase voltages to be provided to the stator;
receive an indication of phase currents flowing in the stator in response to the plurality of phase voltages;
determine an angular position of the impeller based at least in part on the plurality of phase currents; and
adjust the plurality of phase voltages provided to the stator based on the angular position of the impeller.

* * * * *